United States Patent [19]

Ogino

[11] Patent Number: 5,247,339

[45] Date of Patent: * Sep. 21, 1993

[54] FLOW IMAGING CYTOMETER

[75] Inventor: Shinichi Ogino, Hyogo, Japan

[73] Assignee: TOA Medical Electronics Co., Ltd., Japan

[ * ] Notice: The portion of the term of this patent subsequent to Oct. 27, 2009 has been disclaimed.

[21] Appl. No.: 755,302

[22] Filed: Sep. 5, 1991

[30] Foreign Application Priority Data

Feb. 27, 1991 [JP] Japan .................................. 3-033151

[51] Int. Cl.⁵ ..................... G01N 33/48; G01N 21/64; G06K 9/20
[52] U.S. Cl. .................................. 356/73; 250/461.2; 356/23; 356/39; 356/417
[58] Field of Search ....................... 356/23, 39, 72, 73, 356/318, 417; 250/461.2; 382/6

[56] References Cited

U.S. PATENT DOCUMENTS

| | | | |
|---|---|---|---|
| 3,826,364 | 7/1974 | Bonner et al. | 356/73 |
| 4,243,318 | 1/1981 | Stohr | 356/39 |
| 4,338,024 | 7/1982 | Bolz et al. | 356/23 |
| 4,573,796 | 3/1986 | Martin et al. | 356/318 |
| 4,643,566 | 2/1987 | Ohe et al. | 356/317 |
| 4,786,165 | 11/1988 | Yamamoto et al. | 356/23 |
| 5,053,626 | 10/1991 | Tillotson | 250/458.1 |
| 5,159,397 | 10/1992 | Kosaka et al. | 356/417 |
| 5,159,398 | 10/1992 | Maekawa et al. | 356/73 |

FOREIGN PATENT DOCUMENTS

| | | |
|---|---|---|
| 0466168 | 1/1992 | European Pat. Off. . |
| 2246380 | 12/1973 | Fed. Rep. of Germany . |
| 3705876 | 4/1988 | Fed. Rep. of Germany . |
| 1404628 | 9/1975 | United Kingdom . |

Primary Examiner—Richard A. Rosenberger
Attorney, Agent, or Firm—Pearne, Gordon, McCoy & Granger

[57] ABSTRACT

A flow imaging cytometer, in which an image capturing area for cells traveling in the flow of a specimen solution is constantly monitored to perform cell photography in an efficient manner, is improved so that fluorescent images of cells can be acquired with greater efficiency. Cell particles to be sensed in the specimen are treated with a fluorescent stain, and the specimen solution is irradiated with light from a pulsed light source for exciting fluorescence, and with infrared light constantly for monitoring the passage of cells through the cytometer. When the monitoring light is made to serve also as the light for exciting fluorescence, the specimen flow is continuously irradiated at all times at a low luminance for the purpose of monitoring. Then, when a cell particle of interest is detected, the cell particle is irradiated with a light pulse of high luminance to obtain a still picture of the fluorescence-emitting cell. At detection of the cell, a source of white light can be actuated to acquire a white-light image of the cell.

13 Claims, 10 Drawing Sheets (EXCITING-LIGHT EMISSION TRIGGERING PULSE)

FLOW IMAGING CYTOMETER

BACKGROUND OF THE INVENTION

1. Field of the Invention

This invention relates to an apparatus for forming a particle-containing specimen solution such as blood or urine into a flat sheathed flow, irradiating the flat flow of the specimen solution with pulsed light to obtain a still picture, and applying imaging processing to perform analysis such as classification and enumeration of the particle components contained in the specimen solution. More particularly, the invention relates to a flow imaging cytometer, which is a particle image analyzer, adapted so as to constantly monitor an image capturing area of the flat specimen flow, irradiate the particles with light when they reach the image capturing area, and acquire a fluorescent image and/or image by white light of the particle components in an efficient manner.

2. Description of the Prior Art

A technique known in the art is to subject particles such as stained cells to exciting light and perform analysis such as classification of the particles by detecting fluorescence emitted by the particles. Specific examples of apparatus which employ this technique are flow cytometers and microscopes.

A flow cytometer is capable of detecting the amount of fluorescence emitted by individual particles.

A detailed fluorescent image can be observed by using a microscope. In addition, an arrangement is available in which the fluorescent image obtained is subjected to image processing. Furthermore, the specification of Japanese Patent Application Laid-Open (KOKAI) No. 63-269875 discloses an image capturing apparatus whereby images can be acquired using three types of light, namely ultraviolet light, visible light and infrared light.

An apparatus for acquiring the images of particles flowing as a flat stream and analyzing the particles by image processing is disclosed in the specifications of Japanese Patent Application Laid-Open No. 57-500995 and U.S. Pat. No. 4,338,024.

Further, the present applicant has previously filed an application for an apparatus adapted so as to constantly monitor an image capturing area, detect particles in the flow when they arrive at this area, and acquire images of the particles in efficient fashion.

SUMMARY OF THE INVENTION

Though the conventional flow cytometer exhibits a high processing capability per unit time, the fluorescence from particles can be obtained only as a gross value, and it is not possible to acquire detailed information as to which portions of a particle are emitting fluorescence and the degree of this fluorescence. Though a large quantity of information can be obtained using a microscope, pre-treatment is laborious and a high processing speed cannot be obtained.

Accordingly, an object of the present invention is to provide a flow imaging cytometer which overcomes these difficulties encountered in the prior art.

Another object of the present invention is to provide a flow imaging cytometer having a high analyzing capability and adapted to obtain, efficiently and at high speed, a large quantity of particle information which includes detailed information relating to individual particles.

According to the present invention, the foregoing objects are attained by providing a flow imaging cytometer comprising a flow cell formed to include a flat flow path for causing a specimen solution containing particle components to be sensed to flow as a flat stream, a first light source arranged on a first side of the flow cell for irradiating the specimen solution in the flow cell with pulsed light, first image capturing means arranged on a second side of the flow cell for capturing still pictures of the particle components in the specimen solution irradiated by the first light source, a second light source arranged on the first side of the flow cell for irradiating the specimen solution in the flow cell with light constantly, second image capturing means arranged on the second side of the flow cell for capturing an image of the particle components irradiated by the second light source, processing means for executing prescribed analysis based upon image data from the first and second image capturing means, and control means for detecting the particle components based upon the image data from the second image capturing means, and on the basis of such detection, for actuating the first light source within an image capturing period of the first image capturing means, wherein the particle components to be sensed are treated with a fluorescent stain and the first light source is for exciting fluorescence.

In another aspect of the present invention, the foregoing objects are attained by providing a flow imaging cytometer comprising a flow cell formed to include a flat flow path for causing a specimen solution containing particle components to be sensed to flow as a flat stream, a first light source arranged on a first side of the flow cell for irradiating the specimen solution in the flow cell with light quantity of which is switched, first image capturing means arranged on a second side of the flow cell for capturing still pictures of particle components in the specimen solution irradiated with high-luminance pulsed light from the first light source, second image capturing means arranged on a second side of the flow cell for capturing images of particle components in the specimen solution irradiated continuously with low-luminance light from the first light source, processing means for executing prescribed analysis based upon image data from the first and second image capturing means, and control means for detecting the particle components based upon the image data from the second image capturing means, and on the basis of such detection, for switching the first light source over to irradiation with the high-luminance light, wherein the particle components to be sensed are treated with a fluorescent stain and the first light source is for exciting fluorescence.

Other features and advantages of the present invention will be apparent from the following description taken in conjunction with the accompanying drawings, in which like reference characters designate the same or similar parts throughout the figures thereof.

DETAILED DESCRIPTION OF THE PREFERRED EMBODIMENTS

First Embodiment

Preferred embodiments of the present invention will now be described in detail with reference to the accompanying drawings.

Figure 1:
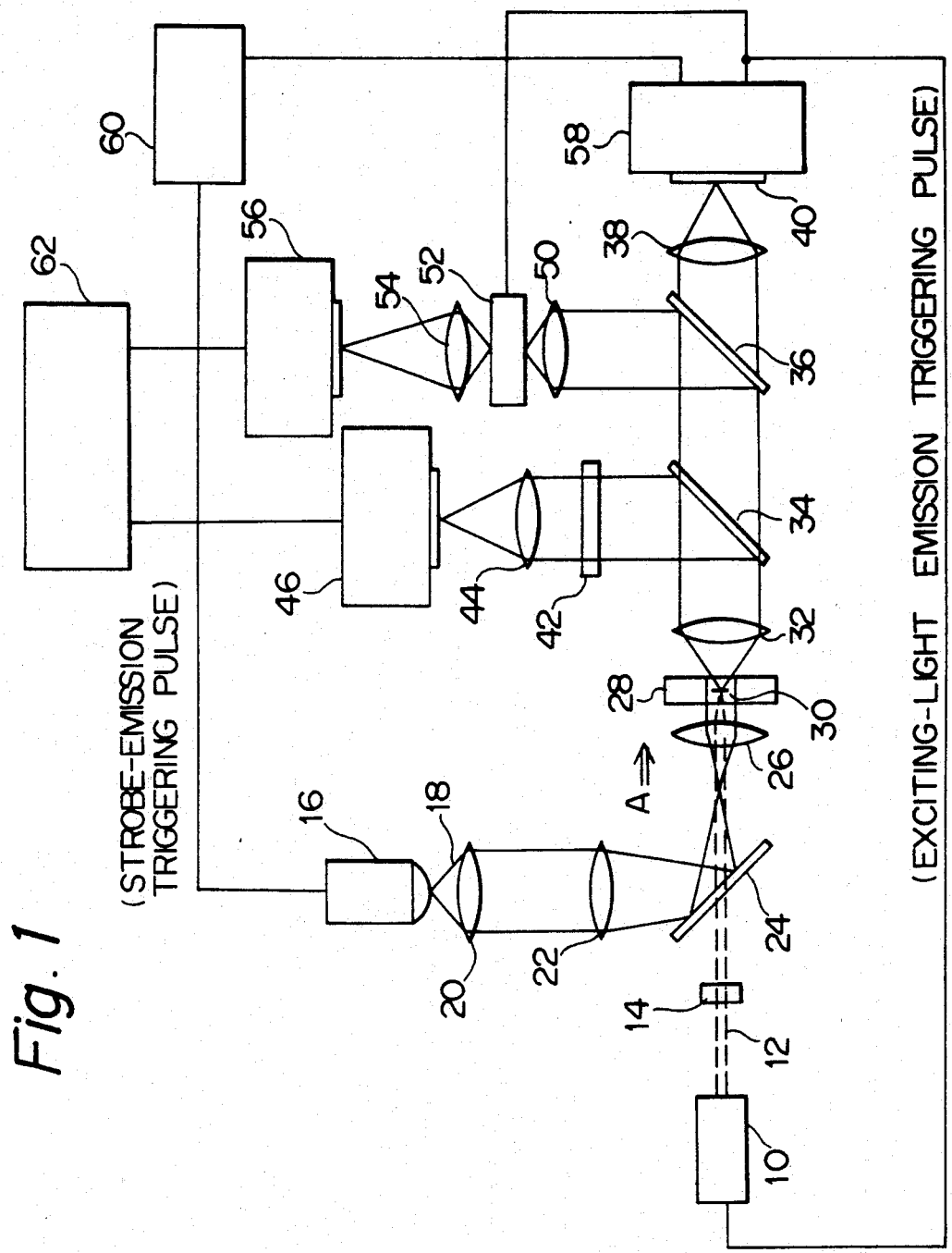
FIG. 1 is a block diagram illustrating the construction of a flow imaging cytometer according to a first embodiment of the present invention.
Figure 6:
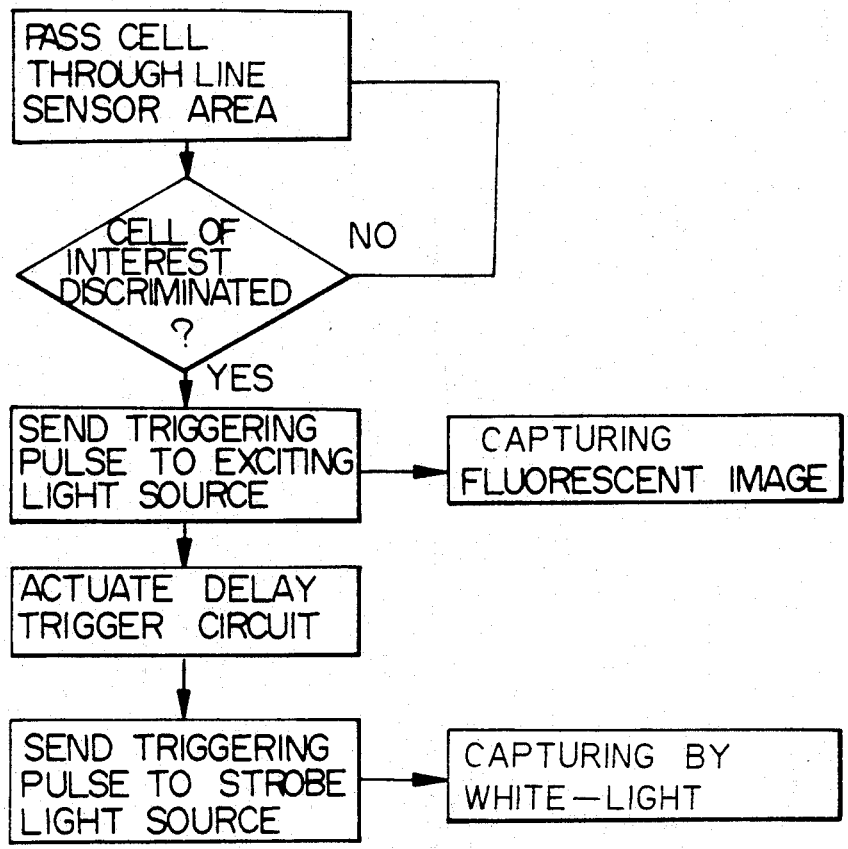
FIG. 6 is a measurement flowchart associated with the flow imaging cytometer of the present invention.

FIG. 1 is a block diagram illustrating the basic construction of a flow imaging cytometer according to a first embodiment of the present invention, and FIG. 6 is a measurement flowchart associated with this cytometer. As shown in FIG. 1, the flow imaging cytometer includes a flow cell 28 in which a stained specimen solution (of blood or urine, etc.) is enveloped by a sheathing liquid and formed into a flat flow. The flow cell 28 has a flat flow path 30 of small thickness and comparatively great width. (As seen in FIG. 1, the flow path 30 is narrow in the horizontal direction and wide in the vertical direction.) The specimen solution along with its sheathing liquid flows through the flat flow path 30 in a direction perpendicular to the plane of the drawing.

Figure 5:
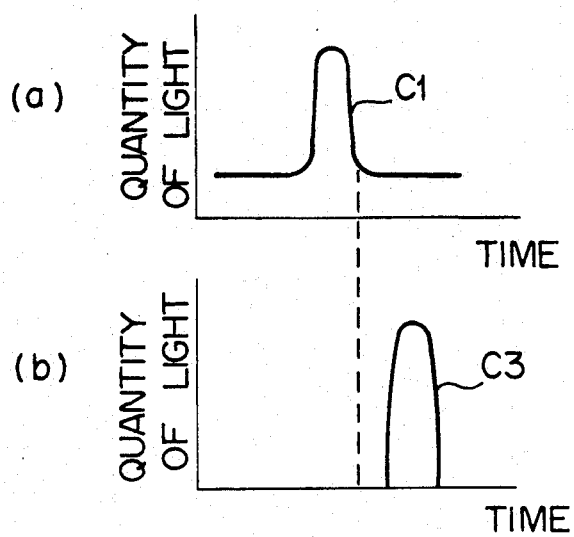
FIG. 5(a) is a diagram showing an example of a luminance curve in particle detection.
FIG. 5(b) is a diagram showing an example of a light-emission pulse for image capturing, the pulse being emitted after detection of a particle.

The apparatus further includes a laser (e.g., an He-Cd laser or Ar+ laser) 10, which serves as a first light source, for exciting fluorescence, and a white-light strobe light source 16, which serves as a third light source, for imaging with white light. The light from each of these light sources enters to a half-mirror 24. The single laser 10 performs a dual function, one of which is to monitor the passage of cell particles through the flow cell 28, and the other of which is to provide light for capturing still pictures of the cells. The apparatus includes first, second and third image capturing means, namely a video camera 56, a CCD line sensor 40 and a video camera 46, respectively. The second image capturing means 40 is for particle detection, and the first and third image capturing means 56, 46 are used in fluorescent image capturing and white-light image capturing. The laser 10 is so adapted that the quantity of light emitted thereby can be varied as required. As indicated by a luminance curve C1 in FIG. 5(a), particle detection ordinarily is performed using a continuous light emission of low luminance. When a particle has been detected, a light pulse is emitted at a high luminance in order to acquire an still picture of the particle, as indicated by curve C3 in FIG. 5(b).

Figure 2:
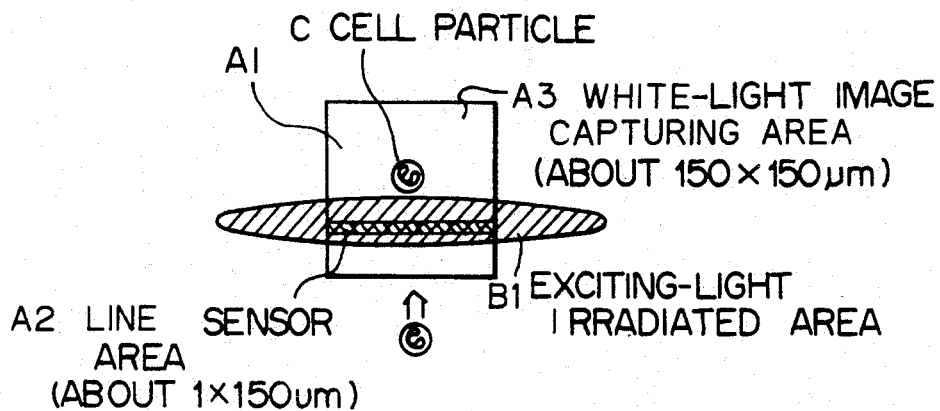
FIG. 2 is a diagram for describing an exciting-light irradiated area and an image capturing area in a flow cell of the cytometer.

FIG. 2 is an enlarged view of a specimen solution flow region as seen from the direction of arrow A in FIG. 1. A linear image capturing area A2 of the second image capturing means 40 is formed so as to cross both an image capturing area A1 of the first image capturing means 56 and an image capturing area A3 of the third image capturing means 47 in a direction substantially perpendicular to the flow of particles.

Light 12 from the laser 10 is acted upon by a light-forming unit 14, which comprises a cylindrical lens, and a condenser lens 26, whereby the flow zone of the specimen solution is irradiated over a small width in the flow direction (though the width is slightly larger than the outer diameter of the particles of interest) and a large width in a direction orthogonal to the flow direction so as to cover the aforesaid image capturing area A2. (In FIG. 1, the specimen flow zone is irradiated over a small width in the direction perpendicular to the plane of the drawing and over a large width in the vertical direction of the drawing.) When the linear image capturing area (also referred to as an "line sensor area) A2 is irradiated with light, the beam spot has the shape of an elongated ellipse. As a result, the light intensity in the image capturing area A2 is rendered uniform to stabilize particle detection. In addition, the light intensity is raised to improve the S/N ratio at fluorescent image capturing.

Of the light which leaves the flow cell 28, exciting light is imaged on the CCD line sensor 40 via an objective lens 32, a half-mirror 34, a dichroic mirror 36 and a projecting lens 38. Voltage conforming to the quantity of light incident upon the CCD line sensor 40 is successively extracted from its output side. On the basis of this signal, a cell flow-through discriminator 58 (which serves also as a pulse controller) determines in real-time whether a particle has arrived for imaging. When a particle is detected, the discriminator/controller 58 immediately outputs a light-emission triggering signal which causes the laser 10 to emit a high-luminance pulse of light. An image intensifier 52 also is rendered operable in response to the light-emission triggering signal from the discriminator/controller 58. Further, in synchronism with this signal, a triggering signal which fires a white-light strobe 16 is produced.

Figure 4:
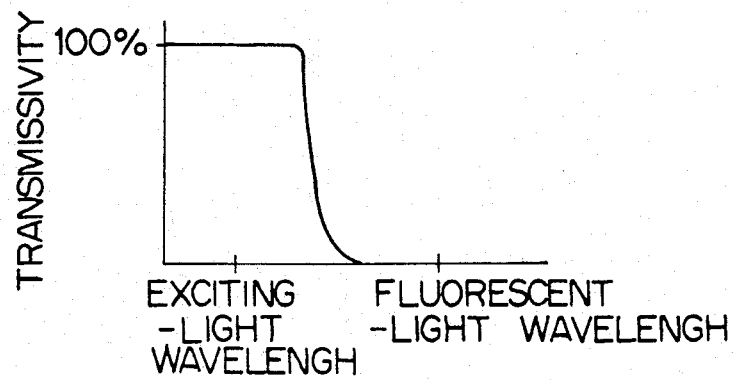
FIG. 4 is a diagram illustrating an example of the characteristic of a dichroic mirror.

FIG. 4 is a characteristic diagram of the dichroic mirror 36.

The high-luminance laser light from laser 10 irradiates the flow cell 28 in the manner described earlier. If an irradiated particle emits fluorescence, the resulting fluorescent image is reflected by the dichroic mirror 36 (though the exciting light itself passes through the dichroic mirror 36 without reflection) and enters to a projecting lens 50, whereby an image is formed on the input surface of the image intensifier 52, which serves as a photoelectric converting imaging device. The image intensifier 52 rendered operable by the aforementioned signal from the discriminator/controller 58, produces a fluorescent image photomultiplied by a factor of $10^3$–$10^6$ in comparison with the input image. The output fluorescent image is captured by the video camera via a relay lens 54 whereby a fluorescent image of a cell particle is obtained. Since the cell flow-through discriminator 58 produces neither the laser triggering signal nor the intensifier drive signal in the absence of particle detection, the image intensifier 52 is not rendered operational at such time and prevents incident light from reaching the video camera 56. For caution's sake, it is permissible to provide an exciting-light removal filter between the dichroic mirror 36 and projecting lens 50.

Figure 3:
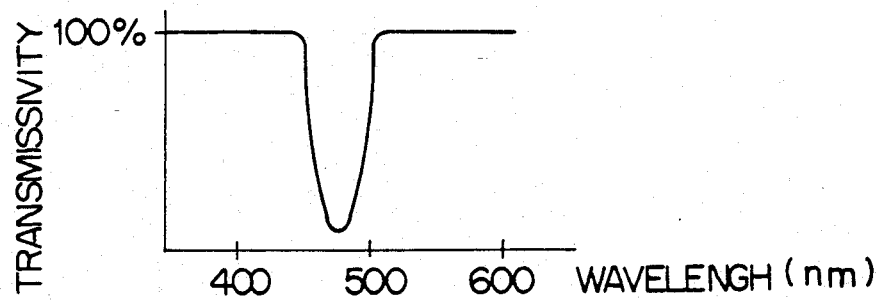
FIG. 3 is a diagram showing the characteristic of a filter for eliminating exciting light.

A delay circuit 60 applies a fixed time delay to the aforementioned triggering signal to obtain the light-emission signal that causes the white-light strobe 16 to fire. Upon receiving this signal, the strobe light source 16 emits a light pulse which follows the high-luminance emission from strobe 10 by a fixed time delay, as indicated by luminance curve C3 in FIG. 5(b). This visible light from the white-light strobe 16 irradiates a portion of the particle-containing flow via a collimator lens 20, a condenser lens 22, a half-mirror 24 and the condenser lens 26. (The irradiation is such that the image capturing areas A1 and A3 in FIG. 2 are covered.) The resulting white-light image from flow cell 28 is formed on the video camera 46 via the objective lens 32, the half-mirror 34, an exciting-light removal filter 42 and an objective lens 44. FIG. 3 is a characteristic diagram of the exciting-light removal filter.

At the time of the high-luminance light pulse emission from laser 10, light in the wave-length region of the exciting light also reaches the CCD line sensor 40 corresponding to the image sensor area when strobe 16 emits a light pulse. However, if an inhibit signal is applied in this interval, the cell flow-through discriminator 58 will not operate erroneously and will not produce an unnecessary signal. To this end, a high-speed electronic shutter can be provided in front of the line sensor 40, as will be described later.

Further, the arrangement of FIG. 1 is such that under conditions set forth below, all particles which flow through the image capturing area A2 can be monitored (with the exception of particles through which the exciting light is transmitted intact). In this case, in the arrangement of FIG. 1, the exciting light emerging from the flow cell 28 is intercepted and the fluorescent light from a particle is separated to form an image on the video camera 46 and on the CCD line sensor 40. As a result, the CCD line sensor 40 forms a fluorescent-light image only. Thus, of the particles that pass through the image capturing area A2, only particles that emit fluorescence can be made the subject of monitoring. In order to select the fluorescent light, use can be made of an exciting-light removal filter or a dichroic mirror, by way of example. To effect separation into fluorescent light, the half-mirror 34 can be employed.

In operation, the one-line scanning period of the line sensor 40 in the apparatus described above is several tens of microseconds. Therefore, if the flow velocity of the specimen solution is given an appropriate value, a fluorescent image and a white-light image can be captured in the respective image capturing areas A1 and A3. Assume that the width of the image capturing area A2 of the CCD line sensor 40 is 1 $\mu$m, the scanning period of the line sensor is 33 $\mu$sec and size of a leukocyte is 15 $\mu$m. If the flow velocity is set at, say, 0.1 m/sec, then the distance traveled by the cell in one scanning interval will be 3.3 $\mu$m. This means that four scans will always be made during transit of the leukocyte through the image capturing area A2 of the line sensor. It is determined by such scanning whether the cell passing through the area A2 is a cell of interest. This determination is performed in real-time. If a cell is determined to be a cell of interest, a triggering pulse is applied to the exciting light source. Assume that the length of time from the start of scanning by the line sensor 40 to the application of the triggering pulse is 50 $\mu$sec. In this period of time the sample will move by about 5 $\mu$m. By making the exciting-light irradiation area about 30 $\mu$m in size, the entirety of the cell will be irradiated with the exciting light. Since it is preferred that the size of the irradiation area be the same as that of the cell of interest to the greatest degree possible, the exciting-light irradiation area and the image sensor capturing area are set depending upon a balance between the signal processing time of the image sensor and the flow velocity of the sheathing liquid. The exciting light and fluorescent light are acted upon by the objective lens 26, half-mirror 34, dichroic mirror 36 and projecting lens 50 in such a manner that only the fluorescent component has its image formed on the photoelectric converting surface of the image intensifier 52. Thereafter, the fluorescent image is intensified by a factor of $10^3$–$10^6$ by the image intensifier 52 to form an image on the fluorescent surface side of the intensifier. This image is formed on the video camera 56 via the relay lens 54. At this time a fluorescent image of the leukocyte appears on the image capturing screen.

After the exciting light source is triggered, the strobe light source 16 is triggered following a suitable delay. In a case where a wavelength of the visible-light region is used as the light source 10 for exciting fluorescence, the time delay should be long enough for the cell of interest (C in FIG. 2) to exit from the exciting-light irradiation area. This is processing for taking a still picture on the outer side of a portion of saturated luminance produced by the exciting light source in the image capturing area. To achieve this, the time delay selected should range from 100 to 300 $\mu$s after triggering of the exciting light. The strobe light from strobe 16 is collimated by the collimator lens 20 and then condensed by the condenser lens 22. The condensed light is reflected by the half-mirror 24 so as to impinge upon the condenser lens 26, whereby the image capturing area is irradiated. The transmitted light is acted upon by the objective lens 32, half-mirror 34, exciting-light removal filter 42 and projecting lens 44, whereby an image is formed on the CCD surface of the video camera 46. A white-light image of the leukocyte appears on the image capturing screen at this time.

By thus adopting the foregoing arrangement, both a white-light image and fluorescent image of a cell of interest can be obtained. By providing a high-speed electronic shutter, which is synchronized to the exciting-light triggering pulse, in front of the image sensor, the influence of the strobe light upon the fluorescent image can be reduced.

In this embodiment of the invention set forth above, only capturing of the fluorescent image is described. However, it is possible to obtain a three-dimensional distribution of the quantity of fluorescence within a cell by using an image processor to process the image obtained from the video camera 56. In addition, a depolarized image of the fluorescent light from a cell can be obtained by using a linearly polarized laser as the exciting light source and arranging a polarizer, which passes a polarized component orthogonal to the polarizing direction of the exciting light, between the dichroic mirror 36 and projecting lens 50 of the optical system for fluorescent image photography. In such case, if visible light is used for the light source which induces fluorescence in this embodiment, then the filter for removing the exciting light on the side of the white-light image capturing system would need to be a filter of the kind shown in FIG. 3, for eliminating wavelengths in the narrow-band region.

Second Embodiment

Figure 7:
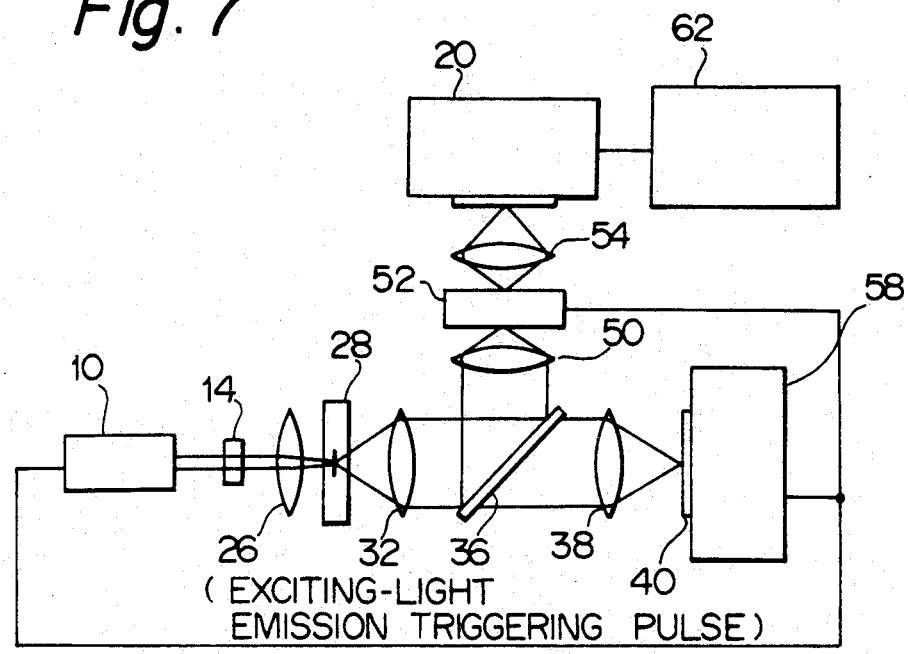
FIG. 7 is a block diagram illustrating the construction of a flow imaging cytometer according to a second embodiment of the present invention.
Figure 8:
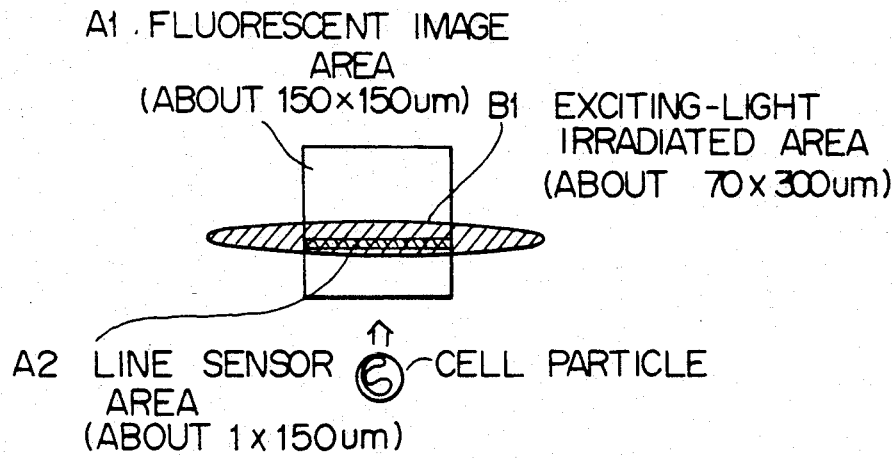
FIG. 8 is a diagram for describing examples of image capturing areas and irradiation areas in a flow cell associated with the cytometer of FIG. 7.

FIG. 7 is a block diagram illustrating a second embodiment of the present invention, which does not possess the white-light image capturing function of the first embodiment. With this arrangement it is still possible to apply particle detection to all particles or only to particles which emit fluorescence. As shown in FIG. 8, there is no area A3 for white-light image capturing.

Third Embodiment

Figure 9:
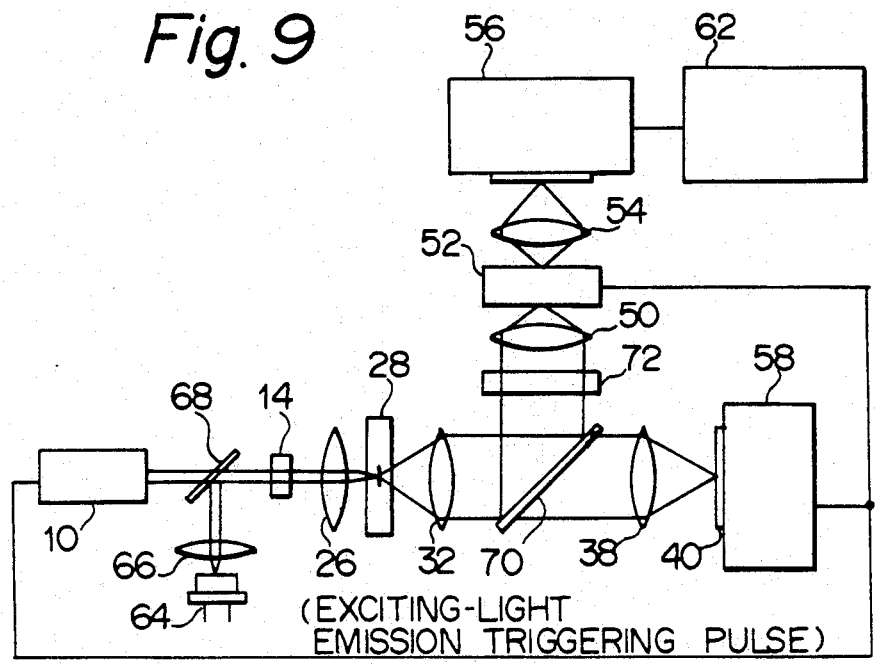
FIG. 9 is a block diagram illustrating the construction of a flow imaging cytometer according to a third embodiment of the present invention.
Figure 14:
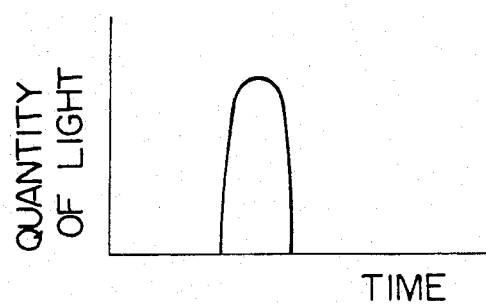
FIG. 14 is a diagram illustrating an example of a pulse for image capturing at the time of particle detection.

FIG. 9 is a block diagram illustrating a third embodiment of the present invention. Here, unlike the first and second embodiments, the light sources are a light source (a second light source) for monitoring particles, and a light source (first light source) for use in image capturing. The second light source is a near infrared semiconductor laser 64, which is associated with a collimator lens 66 and a dichroic mirror 68. The laser 64 emits light at all times. The first light source is the laser 10 for exciting fluorescence as in the first and second embodiments. When a particle is detected, a pulse for image capturing purposes is emitted, as shown in FIG. 14, and the fluorescent image is captured by the video camera 56.

Figure 11:
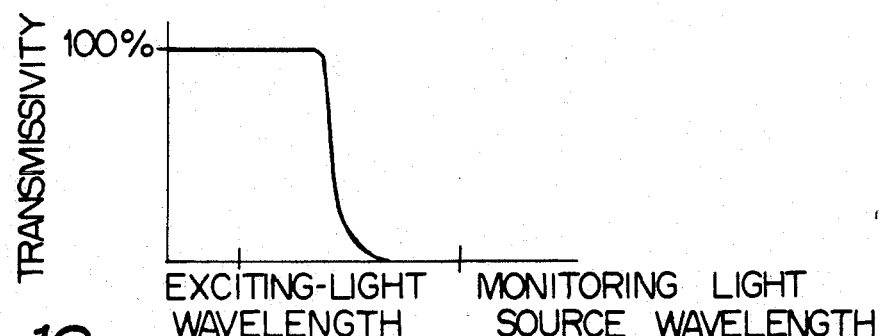
FIG. 11 is a diagram illustrating an example of the characteristic of a dichroic mirror associated with the cytometer of FIG. 9.
Figure 12:
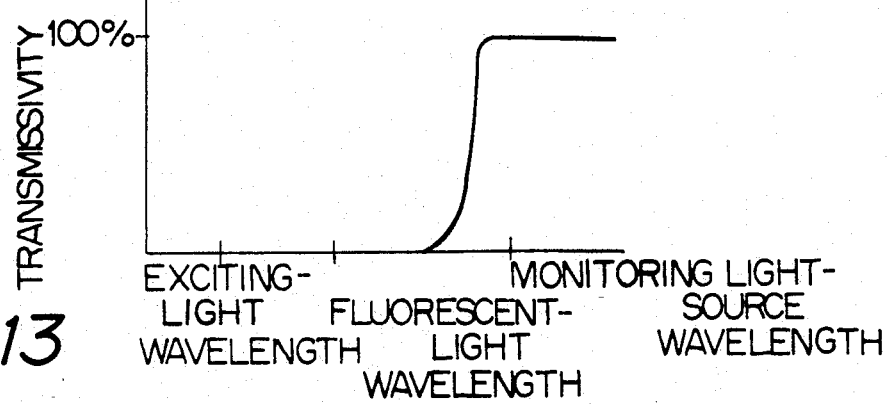
FIG. 12 is a diagram illustrating another example of the characteristic of a dichroic mirror associated with the cytometer of FIG. 9.
Figure 13:
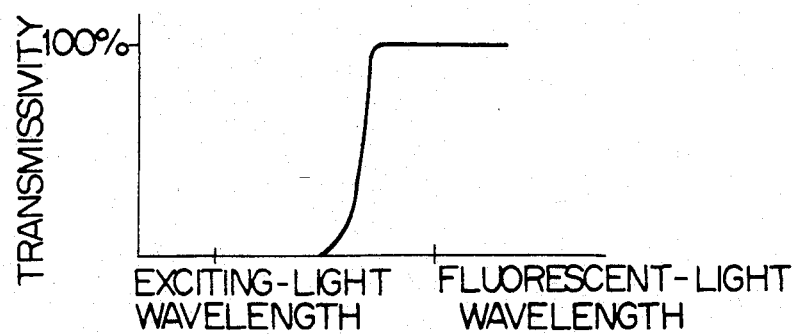
FIG. 13 is a diagram illustrating an example of the characteristic of a filter, associated with the cytometer of FIG. 9, for filtering out exciting light.

FIG. 11 is a characteristic diagram of the dichroic mirror 68, which is capable of separating the exciting light and the monitoring infrared light from each other. FIG. 12 is a characteristic diagram of a dichroic mirror 70 (FIG. 9), which is capable of separating exciting light, fluorescent light and infrared light. FIG. 13 is a characteristic diagram of exciting light removal filter 72 (FIG. 9) for separating exciting light and fluorescent light from each other.

Figure 10:
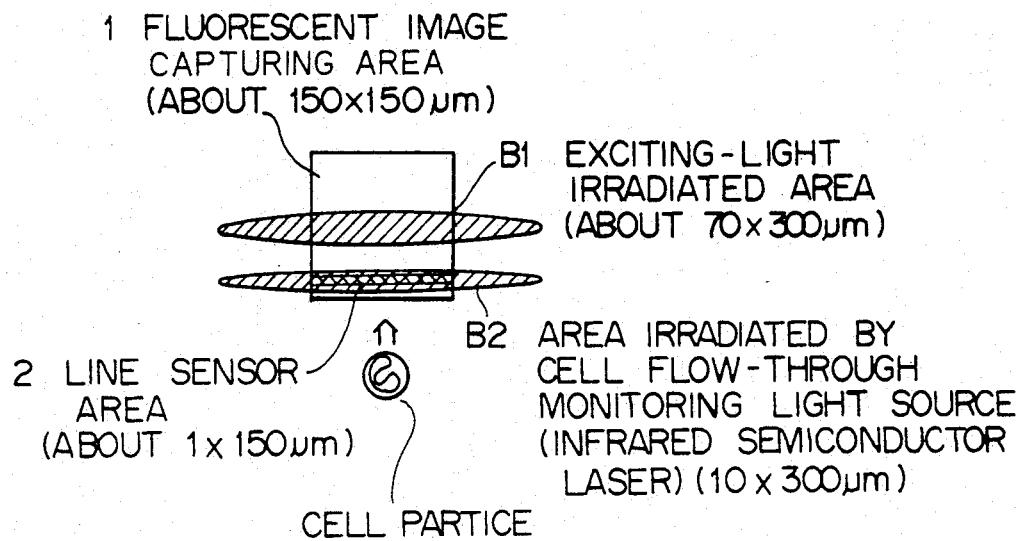
FIG. 10 is a diagram for describing examples of image capturing areas and irradiation areas in a flow cell associated with the cytometer of FIG. 9.

FIG. 10 illustrates image capturing areas. Here a fluorescent-light irradiated area B1 and an infrared-light irradiated area B2 are shown to be separated from each other, although they can overlap each other if desired.

It should be noted that an exciting laser can be used instead of the infrared semiconductor laser 64.

Fourth Embodiment

Figure 15:
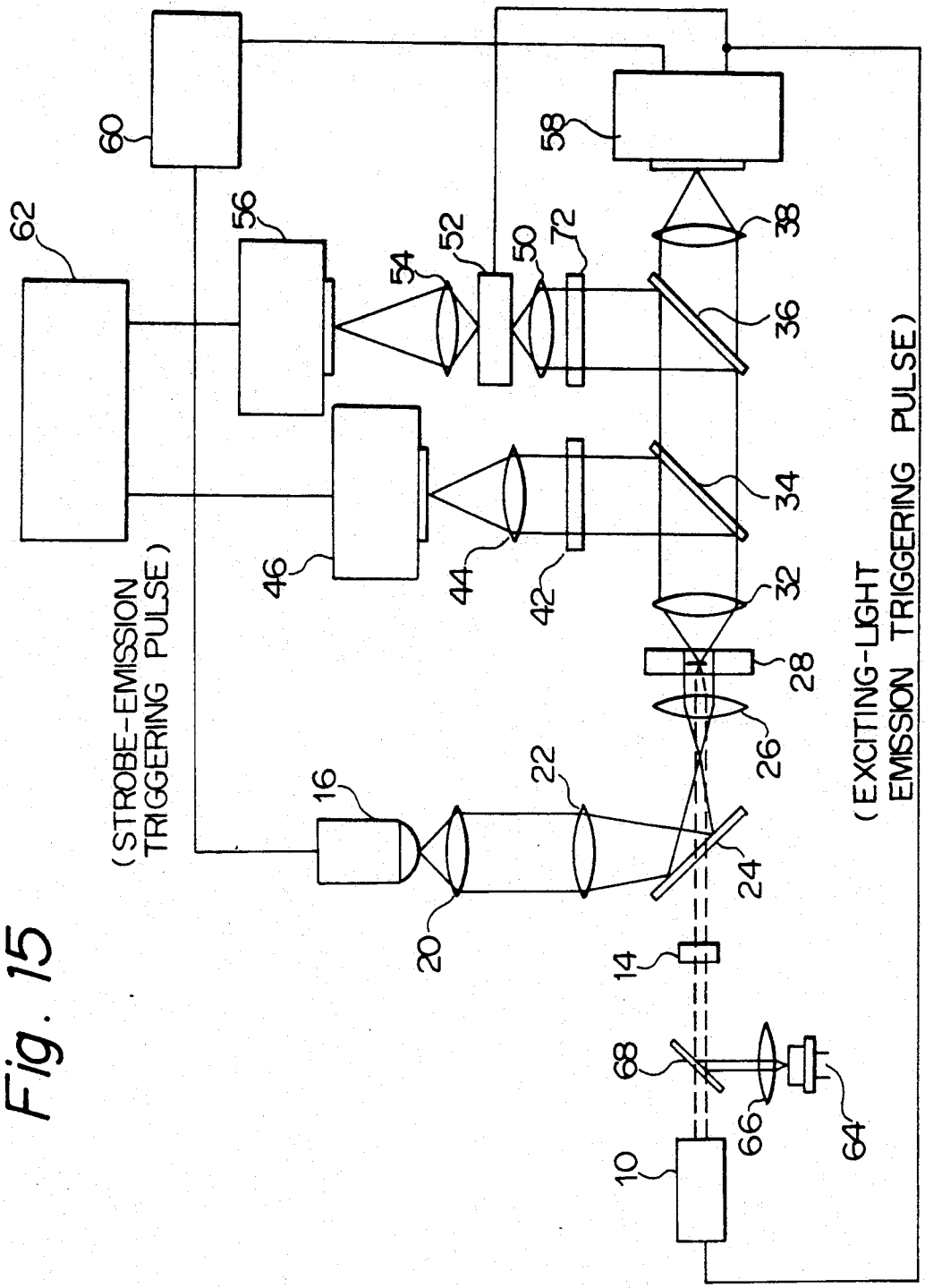
FIG. 15 is a block diagram illustrating the construction of a flow imaging cytometer according to a fourth embodiment of the present invention.
Figure 16:
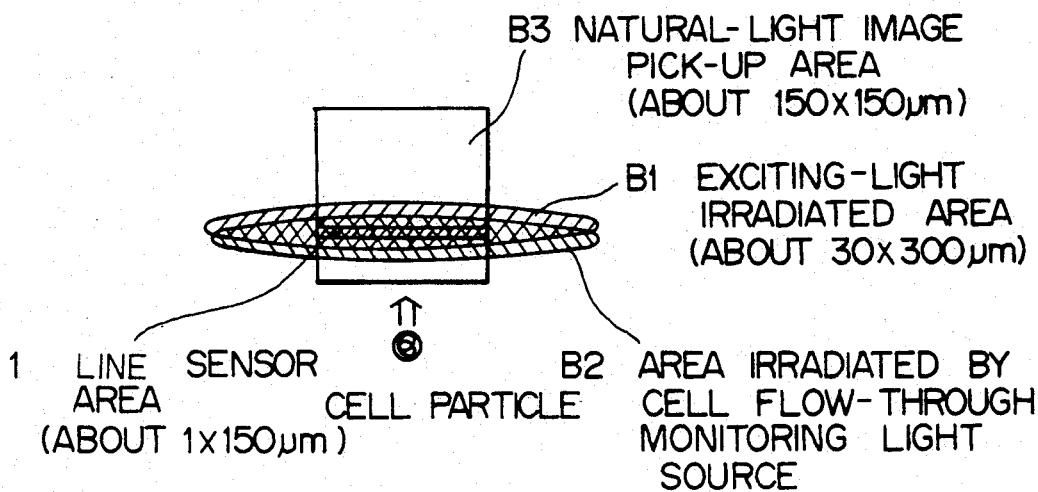
FIG. 16 is a diagram for describing examples of image capturing and irradiation areas in a flow cell associated with the cytometer of FIG. 15.
Figure 18:
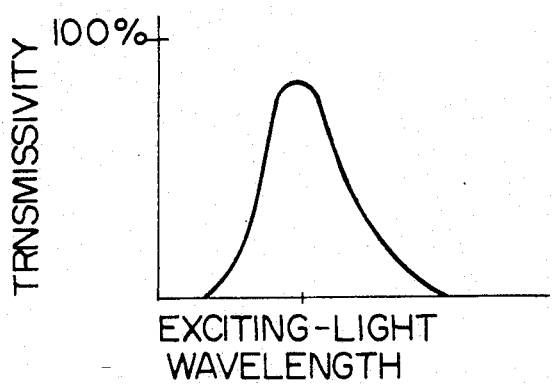
FIG. 18 is a diagram exemplifying the characteristic of an exciting-light selecting (transmitting) filter.

FIG. 15 illustrates a fourth embodiment of the present invention, in which the third embodiment is additionally provided with a white-light image capturing function. To this end, a high-speed electronic shutter 72 synchronized to the exciting light is disposed in front of the image intensifier 52 of the video camera 56 for fluorescent image capturing.

Fifth Embodiment

Figure 17:
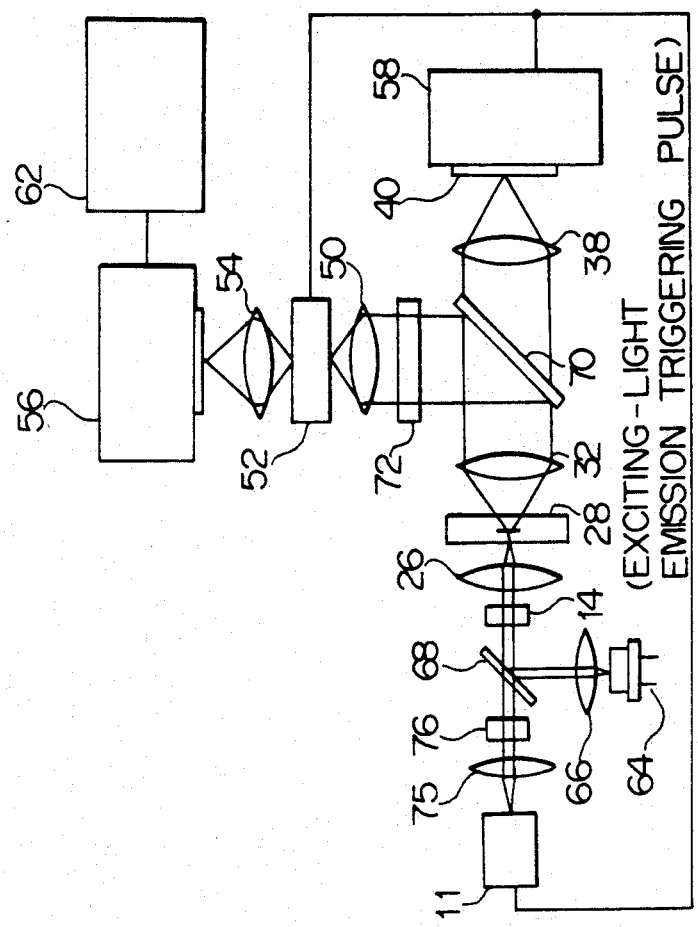
FIG. 17 is a block diagram illustrating the construction of a flow imaging cytometer according to a fifth embodiment of the present invention.

In this embodiment, as shown in FIG. 17, a white-light strobe light source 11, a collimator lens 75 and an exciting-light selecting filter 76 are employed instead of the exciting laser of the first light source in the third embodiment. This makes it possible to perform the same functions. The filter can be exchanged for another when required so that exciting light or fluorescent light can be selected at will. This arrangement is highly versatile since there is no limitation imposed upon the object of measurement.

More specifically, a system capable of photographing a fluorescent image composed of any exciting-light wavelength can be provided by using the white-light source 11, such as a halogen lamp, as the exciting light source, and changing the exciting-light selecting filter 76. In this system, means can be provided for changing an exciting-light removal filter 72 and the exciting-light selecting filter 76 manually or automatically depending upon the staining solution used to treat the measurement sample. As a result, when the CCD line sensor 40 has determined that a particle is a cell of interest, a fluorescent image of this cell can be obtained by the video camera 56 by irradiating the cell with pulsed light from the light source 11.

Sixth Embodiment

Figure 19:
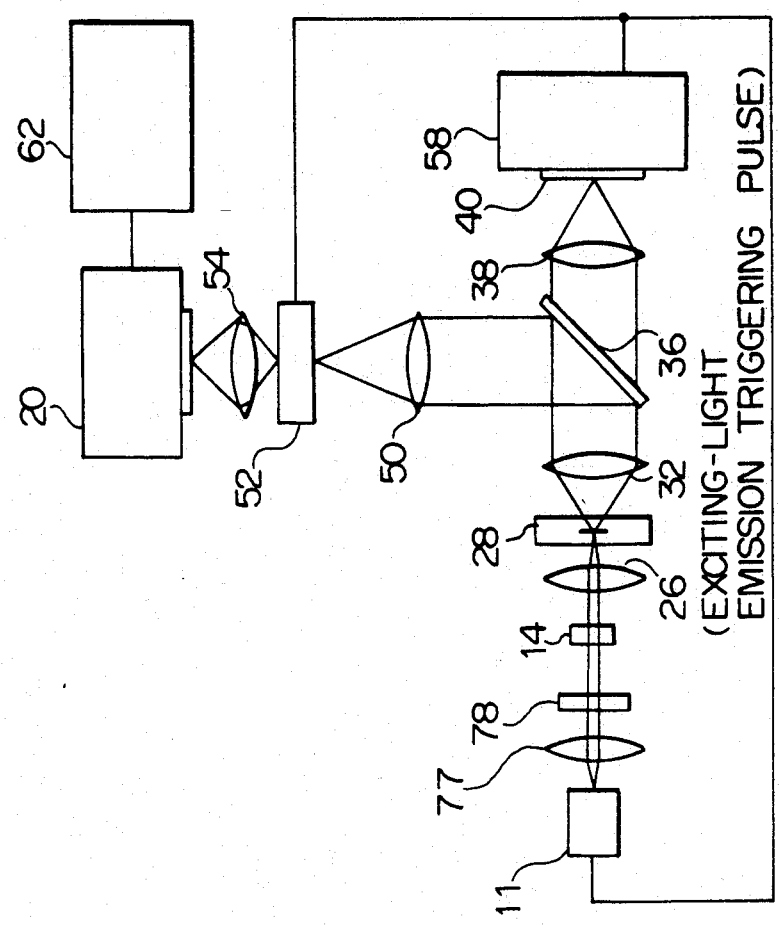
FIG. 19 is a block diagram illustrating the construction of a flow imaging cytometer according to a sixth embodiment of the present invention.

In this embodiment, as shown in FIG. 19, the white-light strobe light source 11, a collimator lens 77 and an exciting-light transmitting filter 78 are employed instead of the exciting laser of the first light source. This makes it possible to perform the same functions.

It is possible to change the type of filter when necessary. In other words, exciting light or fluorescent light can be selected at will, and therefore the arrangement is highly versatile since there is no limitation imposed upon the object of measurement.

In this embodiment, the light source 64 for monitoring cell flow-through in the third embodiment is made to serve also as the exciting light source, thereby simplifying the construction of the system. Passage of cells through the cytometer is monitored by the CCD line sensor 40 by using the exciting light source to perform irradiation normally at low power. Then, when flow-through of a cell of interest has been detected, the cell is irradiated with pulsed light emitted by the exciting light source at high power, thereby making it possible for the video camera to obtain a fluorescent image.

The present invention has the following advantages:
(1) The flow imaging cytometer of the present invention constantly monitors the image capturing area and takes a still picture of a particle when the particle reaches the image capturing area. This makes it possible to acquire fluorescent images of particles accurately and efficiently.
(2) In an arrangement where a white light source is provided, a white-light image can be obtained as well as a fluorescent image. Particle analysis can be performed with greater precision as a result.

(3) The arrangement can be simplified if one light source is made to serve as both a monitoring light source and a photographic light source.

(4) When the second image capturing area for particle detection is made linear in shape, a restriction is placed upon the positions which particles can occupy in an imaged frame. The simplifies subsequent image processing.

(5) In the monitoring of particles, it is possible to switch between the monitoring of all particles and the monitoring solely of particles which emit fluorescence.

(6) Since filters can be interchanged depending upon the subject of measurement, the apparatus can be used with greater universality.

As many apparently widely different embodiments of the present invention can be made without departing from the spirit and scope thereof, it is to be understood that the invention is not limited to the specific embodiments thereof except as defined in the appended claims.

What is claimed is:

1. A flow imaging cytometer comprising:
    a flow cell formed to include a flat flow path for causing a specimen solution containing particle components to be sensed to flow as a flat stream;
    a first light source arranged on a first side of said flow cell for irradiating the specimen solution in said flow cell with light the quantity of which is switched;
    first image capturing means arranged on a second side of said flow cell for capturing still pictures of particle components in the specimen solution irradiated with high-luminance pulsed light from said first light source;
    second image capturing means arranged on a second side of said flow cell for capturing images of the particle components in the specimen solution irradiated continuously with low-luminance light from said first light source;
    processing means for executing prescribed analysis based upon image data from said first and second image capturing means; and
    control means for detecting the particle components based upon the image data from said second image capturing means, and on the basis of such detection, switching said first light source over to irradiation with the high-luminance light, wherein the particle components to be sensed are treated with a fluorescent stain and said first light source is for exciting fluorescence.

2. The flow imaging cytometer according to claim 1, further comprising:
    a third light source arranged on a first side of said flow cell for irradiating the specimen solution in said flow cell with pulsed white light; and
    third image capturing means arranged on a second side of said flow cell for capturing still pictures of the particle components in the specimen solution irradiated by said third light source;
    said control means for detecting the particle components based upon the image data from said second image capturing means, and on the basis of such detection, for switching said first light source over to irradiation with the high-luminance light and actuating said third light source after respective prescribed time delays.

3. The flow imaging cytometer according to claim 2, wherein said first and third image capturing means each has a two-dimensional image capturing area on the flow of the specimen solution, said second image capturing means has a linear image capturing area on the flow of the specimen solution, and the image capturing area of said second image capturing means is formed so as to cross the flow of the specimen solution within the image capturing areas of said first and third image capturing means.

4. The flow imaging cytometer according to claim 1, wherein said first image capturing means has a two-dimensional image capturing area on the flow of the specimen solution, said second image capturing means has a linear image capturing area on the flow of the specimen solution, and the image capturing area of said second image capturing means is formed so as to cross the flow of the specimen solution within the image capturing area of said first image capturing means.

5. The flow imaging cytometer according to claim 4 or 3, further comprising means for forming the irradiating light from said first light source into an elongated elliptical shape.

6. A flow imaging cytometer comprising:
    a flow cell including a flat flow path for causing a specimen solution containing particle components to be sensed to flow as a flat stream, said particle components being treated with a fluorescent stain;
    a first light source arranged on a first side of said flow cell for irradiating the specimen solution in said flow cell with fluorescence exciting pulsed light;
    first image capturing means arranged on a second side of said flow cell for capturing still pictures of the particle components in the specimen solution irradiated by said first light source;
    a second light source arranged on the first side of said flow cell for irradiating the specimen solution in said flow cell with light constantly;
    second image capturing means arranged on the second side of said flow cell for capturing images of the particle components irradiated by said second light source,
    processing means for executing prescribed analysis based upon image data from said first and second image capturing means; and
    control means for detecting the particle components based upon the image data from said second image capturing means, and, on the basis of such detection, actuating said first light source within an image capturing period of said first image capturing means, wherein said first image capturing means has a two-dimensional image capturing area on the flow of the specimen solution, said second image capturing means has a linear image capturing area on the flow of the specimen solution, and the image capturing area of said second image capturing means is formed so as to cross the flow of the specimen solution within the image capturing area of said first image capturing means.

7. The flow imaging cytometer according to claim 6, wherein said second light source emits infrared light.

8. The flow imaging cytometer according to claim 6, wherein said second light source emits exciting light for exciting fluorescence.

9. The flow imaging cytometer according to claim 6, further comprising means for forming the irradiating light from said second light source into an elongated elliptical shape.

10. The flow imaging cytometer according any one of claims 6 to 9, further comprising:
- a third light source arranged on the first side of said flow cell for irradiating the specimen solution in said flow cell with pulsed white light;
- an electronic shutter means provided in front of the first image capturing means; and
- a third image capturing means arranged on the second side of said flow cell for capturing still pictures of the particle components in the specimen solution irradiated by said third light source;
- said third image capturing means having a two-dimensional image capturing area on the flow of the specimen solution, an image capturing area of the first image capturing means being formed so as to cross an image capturing area of the second image capturing means, and the image capturing area of said second image capturing means being formed so as to cross the flow of the specimen solution within the image capturing area of said first and third image capturing means, and
- said control means detecting the particle components based upon the image data from said second image capturing means, and, on the basis of such detection, actuating said first and third light sources after respective prescribed time delays within image capturing periods of said first and third image capturing means respectively.

11. A flow imaging cytometer comprising:
- a flow cell including a flat flow path for causing a specimen solution containing particle components to be sensed to flow as a flat stream, said particle components being treated with a fluorescent stain;
- a first light source arranged on a first side of said flow cell for irradiating the specimen solution in said flow cell with fluorescence exciting pulsed light;
- first image capturing means arranged on a second side of said flow cell for capturing still pictures of the particle components in the specimen solution irradiated by said first light source;
- second image capturing means arranged on a second side of said flow cell for capturing images of the particle components in the specimen solution irradiated continuously with low-luminance light from said first light source;
- processing means for executing prescribed analysis based upon image data from said first and second image capturing means; and
- control means for detecting the particle components based upon the image data from said second image capturing means, and, on the basis of such detection, switching said first light source over to irradiation with the high-luminance light, wherein said first image capturing means has a two-dimensional image capturing area on the flow of the specimen solution, said second image capturing means has a linear image capturing area on the flow of the specimen solution, and the image capturing area of said second image capturing means is formed so as to cross the flow of the specimen solution within the image capturing area of said first image capturing means.

12. The flow imaging cytometer according to claim 11, further comprising means for forming the irradiating light from said first light source into an elongated elliptical shape.

13. The flow imaging cytometer according to any one of claims 11 or 12, further comprising;
- a third light source arranged on a first side of said flow cell for irradiating the specimens solution in said flow cell with pulsed white light;
- third image capturing means arranged on a second side of said flow cell for capturing white light still pictures of the particle components in the specimen solution irradiated by said third light source; and
- an electronic shutter means provided in front of the first image capturing means;
- said third image capturing means having a two-dimensional image capturing area on the flow of the specimen solution, an image capturing area of the first image capturing means being formed so as to cross an image capturing area of the third image capturing means, and the image capturing area of said second image capturing means being formed so as to cross the flow of the specimen solution within the image capturing areas of said first and third image capturing means,
- said control means for detecting the particle components based upon the image data from said second image capturing means, and, on the basis of such detection, switching said first light source over to irradiation with the high-luminance light and actuating said third light source after respective minimum time delays and passing light at said shutter means during emitting the high-luminance light of the first light source and shielding light at said shutter means during emitting the light of the third light source.

* * * * *